United States Patent
Lund et al.

(10) Patent No.: US 7,351,912 B2
(45) Date of Patent: Apr. 1, 2008

(54) MEDICAL CABLE

(75) Inventors: Peter A. Lund, Nashua, NH (US);
Marc Cordaro, Sudbury, MA (US);
Michael Parascandola, Londonderry, NH (US); Gary A. Freeman, Newton Center, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 11/054,843

(22) Filed: Feb. 10, 2005

(65) Prior Publication Data
US 2006/0178030 A1    Aug. 10, 2006

(51) Int. Cl.
*H01B 7/00*   (2006.01)
(52) U.S. Cl. ............... 174/110 R; 174/113 R
(58) Field of Classification Search ............ 174/36, 174/74 R, 110 R, 113 R, 117 R, 117 F, 117 FF, 174/113 C
See application file for complete search history.

(56) References Cited

U.S. PATENT DOCUMENTS

| | | | | |
|---|---|---|---|---|
| 3,715,458 A | * | 2/1973 | Bayes et al. ............ | 174/113 R |
| 4,353,372 A | * | 10/1982 | Ayer ........................ | 600/393 |
| 4,761,519 A | * | 8/1988 | Olson et al. .............. | 174/107 |
| D363,989 S | | 11/1995 | Crouse | |
| D366,528 S | | 1/1996 | Crouse et al. | |
| 5,491,299 A | * | 2/1996 | Naylor et al. ............. | 174/36 |
| 5,552,565 A | * | 9/1996 | Cartier et al. ............ | 174/117 F |
| 5,937,950 A | * | 8/1999 | Adams et al. ............ | 174/72 R |
| 5,976,070 A | * | 11/1999 | Ono et al. ................ | 600/110 |
| 6,247,963 B1 | * | 6/2001 | Rattner .................... | 439/502 |
| 6,841,734 B2 | * | 1/2005 | Goldlust et al. ......... | 174/102 R |
| 2003/0056971 A1 | * | 3/2003 | Wechsler ................. | 174/113 R |
| 2003/0111255 A1 | * | 6/2003 | Buck et al. .............. | 174/113 R |
| 2004/0065469 A1 | * | 4/2004 | Goldlust et al. ......... | 174/103 |
| 2005/0061536 A1 | * | 3/2005 | Proulx ..................... | 174/102 R |

FOREIGN PATENT DOCUMENTS

JP        04-319205 A  *  4/1991

* cited by examiner

*Primary Examiner*—William H. Mayo, III
(74) *Attorney, Agent, or Firm*—Fish & Richardson P.C.

(57) ABSTRACT

A cable configured for use between a medical device and a subject, includes a first end configured to connect to the medical device, a second end configured to connect to the subject, and a single elongated body between the first and second ends. The body contains a first set of conductors configured to perform a therapeutic function, and a second set of conductors configured to perform a first monitoring function.

27 Claims, 4 Drawing Sheets

MEDICAL CABLE

TECHNICAL FIELD

The invention relates to a medical cable.

BACKGROUND

A defibrillator is a medical device that is capable of performing one or more therapeutic functions on a subject. For example, a defibrillator can provide therapy to the subject's heart by delivering defibrillation pulses to normalize an irregular heart rhythm and pacing pulses to regulate the heart's rate.

In addition, certain defibrillators are also capable of performing one or more monitoring or sensing functions to assist the cardiac therapy. These multi-function defibrillators can measure certain vital signs of the subject and provide an indication of the measurements. For example, these defibrillators may be able to monitor the percentage of the subject's hemoglobin that is saturated with oxygen ($SpO_2$ monitoring), the levels of carbon dioxide expired by the subject ("end tidal $CO_2$" ($EtCO_2$) monitoring), the subject's blood pressure (via non-invasive blood pressure (NIBP) or invasive blood pressure (IBP) monitoring), the electrical voltage in the subject's heart (in the form of an electrocardiogram (ECG)), multiple-lead ECG, and/or the subject's temperature. The defibrillators may also include cardiopulmonary resuscitation (CPR) assistance via an accelerometer or other technology, providing an indication of the depth and rate at which compressions should be applied.

A defibrillator that is capable of providing a therapeutic function and a monitoring function may include a single housing and one or more cables that are connectable to the housing. The housing contains the circuitry and other components of the defibrillator. The cables provide the interface between the housing and the subject during use. There may be one cable associated with the one or more therapeutic functions and one cable for each of the monitoring functions. As a result, there may be more than eight cables that extend between the housing and the subject. Users of all of these functions, along with users of a subset of these functions often complain of the many individual cables that may need to be untangled to connect a patient to a defibrillator in an emergent situation. In this situation, the user is pressed for time and may need to connect the patient quickly to administer life-saving therapy.

In addition, when the defibrillator is on a crash cart or being held by the user, there are many cables that go between the defibrillator and the patient, causing potential entanglement as a patient is transported. This can impede the transport to a critical care area where the patient can receive a full array of treatment. As well, when a patient is transported up and down stairs or in tight quarters (as often occurs in the EMS environment), the user may want to quickly disconnect the patient from the defibrillator temporarily to avoid any potential entanglement. The customary manner of disconnection is to disconnect the cables at the defibrillator end. With current devices,. this may require disconnection of a multitude of cables. In a resuscitation event, when treating a patient in cardiac arrest, the cable providing the therapeutic electrical therapy (e.g., the defibrillation therapy) must not have its functionality compromised. Additionally, close proximity of high voltage leads to low voltage monitoring signals can often corrupt the sensitive low voltage signals. U.S. Pat. Nos. 5,491,299, D363,989 and D366,528 describe a cable with multiple conductors in a flexible multi-parameter patient cable, but these references do not provide for a means of inclusion of conductors providing therapeutic electrical energy.

SUMMARY

In a first aspect, the invention features a cable configured for use between a medical device and a subject, including a first end configured to connect to the medical device, a second end configured to connect to the subject, and a single elongated body between the first and second ends. The body contains a first set of conductors configured to perform a therapeutic function, and a second set of conductors configured to perform a first monitoring function.

Preferred implementations of this aspect of the invention may incorporate one or more of the following features. The therapeutic function is defibrillation and/or cardiac pacing. The first set of conductors and/or the second set of conductors is electromagnetically shielded. The first monitoring function is selected from the group consisting of oxygen monitoring, carbon dioxide monitoring, blood pressure monitoring, cardiopulmonary resuscitation assistance, electrocardiographing, and temperature monitoring. The elongated body contains multiple sets of conductors configured to perform different monitoring functions. The cable is configured to perform defibrillation, pacing, oxygen monitoring, cardiopulmonary resuscitation assistance, and electrocardiographing. The cable further includes a filler material extending along the length of the elongated body. The first set of conductors has a first width, the second set of conductors has a second width different than the first width, and the filler material is between the first and second sets of conductors. The body has a non-circular cross section. The first end has a single connector configured to connect to the medical device. The first end has a plurality of connectors configured to connect to the medical device. The body has a length of from about six to about eight feet. The cable further includes a fastener attachable to the cable.

In a second aspect, the invention features a cable configured for use between a medical device and a subject, including a first end configured to connect to the medical device, a second end configured to connect to the subject, and a single elongated body between the first and second ends. The body contains a first set of conductors configured to perform cardiopulmonary resuscitation assistance, and second set of conductors configured to perform a first monitoring function.

Preferred implementations of this aspect of the invention may incorporate one or more of the following features. The first set of conductors is configured to connect to an accelerometer. The first monitoring function is selected from the group consisting of oxygen monitoring, carbon dioxide monitoring, blood pressure monitoring, electrocardiographing, and temperature monitoring. The second set of conductors is electromagnetically shielded. The body contains multiple sets of conductors configured to perform different monitoring functions. The cable further includes a filler material extending along the length of the body. The body has a non-circular cross section. The first end has a single connector configured to connect to the medical device. The first end has a plurality of connectors configured to connect to the medical device. The body has a length of from about six to about eight feet.

In a third aspect, the invention features a method of providing therapy to and monitoring a subject, the method includes delivering a therapeutic electrical pulse and monitoring a parameter of the subject through a single cable connected to and extending between the subject and a medical device.

Preferred implementations of this aspect of the invention may incorporate one or more of the following features. The electrical pulse is a defibrillation pulse or a cardiac pacing pulse. The parameter is selected from the group consisting of oxygen monitoring, carbon dioxide monitoring, blood pressure monitoring, cardiopulmonary resuscitation assistance, electrocardiographing, and temperature monitoring.

Among the many advantages of the invention (some of which may be achieved only in some of its various aspects and implementations) are the following. The multi-function cable, as described herein, integrates one or more therapy wires with one or more monitoring wires in a single trunk cable. This integration can eliminate the multitude of cables that extend between the subject and the defibrillator for the majority of the cable length, thereby allowing the cable to be easily managed. For example, the multi-function cable can reduce the total length and volume of cables that need to be stored. As a result, cable storage requires less time and effort because there is less overall length of cable to bundle, and the volume needed to store the cable is reduced. Cable entanglement is also reduced.

The cable can also be easily deployed. Deployment of the cable to connect the subject to the defibrillator may take less time because there is less length of cable to unbundle and the occurrence of cable entanglement is reduced. The cable can be quickly connected to the defibrillator and to the patient, and quickly disconnected (e.g., from the defibrillator when the patient is being transported through tight spaces).

At the same time, the cable has good mechanical properties and electrical performance. The cable is constructed to be flexible and durable. The cable is also constructed to experience low electromagnetic interference, and to have a low total capacitance, thereby lowering the risk of unacceptable patient leakage current.

Other aspects, features and advantages of the invention will be found in the detailed description, drawings, and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
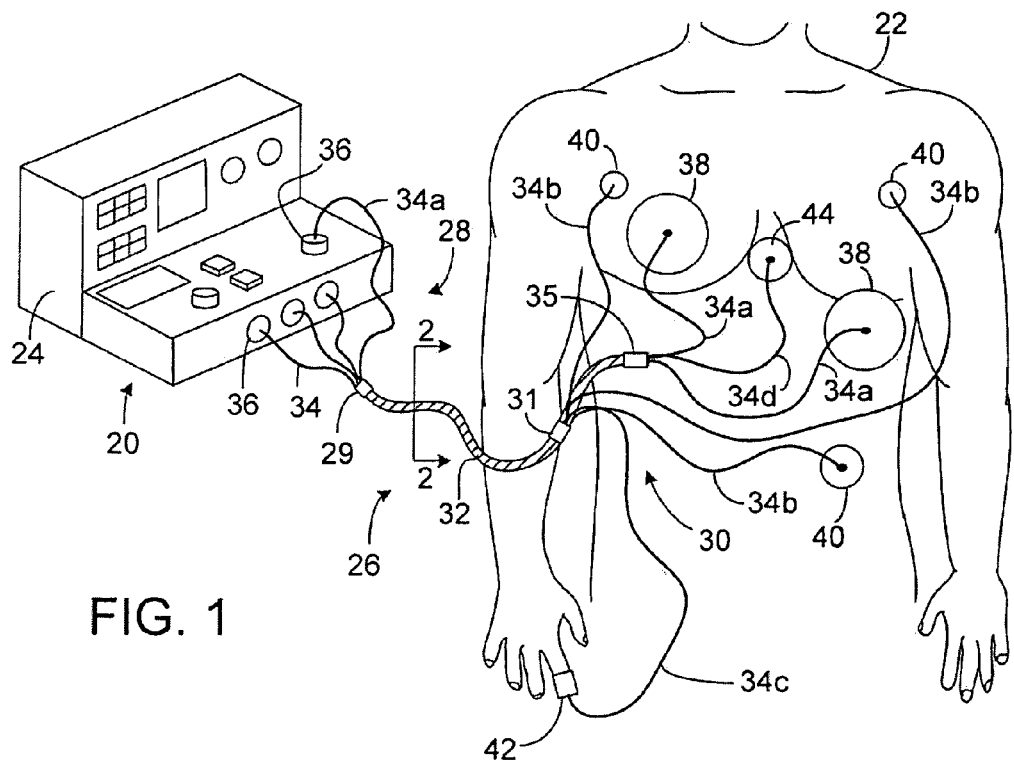
FIG. 1 is a diagrammatic view of an implementation of a cable during use.

Referring to FIG. 1, a multi-function medical device 20 is shown as used on a subject 22. As shown, medical device 20 includes a housing 24 that contains the circuitry and other components of the medical device, and a cable 26 that can be connected to the housing. Cable 26 includes a single trunk cable 32 that extends between two yokes 29, 31, from a device end 28 to a subject end 30. At device end 28, cable 26 includes a plurality of wires 34 that are attached to connectors 36 configured to connect to housing 24, and to trunk cable 32 at yoke 29. Yoke 29 is a junction where wires 34 come together and join with trunk cable 32. In some implementations, yoke 29 includes a computer board with a plastic overmold along with strain reliefs on wires 34. Wires 34 are connected to wires in trunk cable 32 that extend along the trunk cable and toward yoke 31 at subject end 30. At yoke 31, wires 34 are connected to wires 34a-34d, which diverge from yoke 31. As shown, wires 34c, which are configured to connect to finger clip 42 for $SpO_2$ measurements, and wires 34b, which are configured to connect to ECG electrodes 40, extend from yoke 31. Wires 34a, which are configured to connect to electrodes 38 for delivering defibrillation and/or pacing pulses, and wire 34d, which are configured to connect to an accelerometer 44 or other technology (such as AutoPulse CPR) for CPR assistance, extend past yoke 31 to a connector 35 that electrically connects with electrodes 38 and accelerometer 44. In some implementations, wires 34a-34d have a length (e.g., about two feet) that allows the attachments to reach the appropriate area of subject 22 when yoke 31 is placed mid-body. In other implementations, one or more of the wires 34 extend continuously from connectors 36 to their selected attachments at subject end 30 as unitary wire(s), i.e., without any connections necessary at yokes 29, 31. To protect wires 34, a plastic or rubber overmold can be formed to seal the wires where they converge at an end of trunk cable 32.

As indicated above, medical device 20 is a multi-function defibrillator that is capable of performing one or more therapeutic functions and one or more monitoring functions. As used herein, a therapeutic function is an electrical treatment capable of altering a detectable physiological function or causing a detectable physiological response in the subject. In implementations of a therapeutic function, a current of greater than about 20 milliamps is applied to the subject. For example, during therapy, medical device 20 is capable of providing electrical pulses for defibrillation and/or cardiac pacing. Physiological pacing capture typically occurs above about 65 milliamps, and defibrillation currents are much higher and in the magnitude of amps. In contrast, during a monitoring function, medical device 20 measures and displays a selected parameter (such as a vital sign) of the subject, without altering a physiological function or causing a physiological response. For example, medical device 20 can sense and display oxygen levels ($SpO_2$) and heart voltages (ECG), and provide CPR assistance. Other monitoring functions include measuring blood pressure (NIBP and IBP), carbon dioxide levels ($EtCO_2$), carbon monoxide levels, blood gases, and temperature. Monitoring functions, such as SpO2, EtCO2, NIBP and IBP do not intentionally pass current, but in some implementations, during monitoring, device 20 may pass a low current (e.g., less than about one milliamp) through the subject. For example, the impedance measurement associated with ECG lead-off detection may apply a current of about 0.7 milliamps to the patient at about 70 kHz. An example of a multi-function medical device is the M Series defibrillator, available from ZOLL Medical (Chelmsford, Mass.).

Cable 26 is configured to provide the therapeutic function(s) and the monitoring function(s) through a single cable. More specifically, contained within trunk cable 32, cable 26 includes an assembly of wires that are capable of providing the functions. Adding multiple wires into one cable, however, may cause interference between functions and increase the total capacitance of the cable. The capacitance increase is due to the shielding that is implemented to electrically isolate the monitoring and therapeutic functions, for example, to reduce such interference among the wires and to provide clean signals. Interference and capacitance can also be reduced by increasing the mechanical separation between the functions, but doing so may create a big and unwieldy cable. A high capacitance can increase the risk of unacceptable patient leakage current and create a potentially dangerous condition, for example, if a subject contacts ground during use and creates a fault condition that allows current to pass through the subject. Accordingly, wires 34 are generally arranged to reduce the total capacitance of the cable, particularly capacitance between patient-connected circuits such as defibrillation/pacing and ECG and wires connected to system ground (such as control lines). In some implementations, cable 26 has a total capacitance associated with the defibrillation/pacing circuit of less than about 600 picofarads in an 8.5 foot cable, preferably less than about 500 picofarads. To reduce interference, wire(s) that are most sensitive to noise may be spaced as much as possible from wire(s) that cause the most noise, while still staying within a desired volume.

Figure 2:
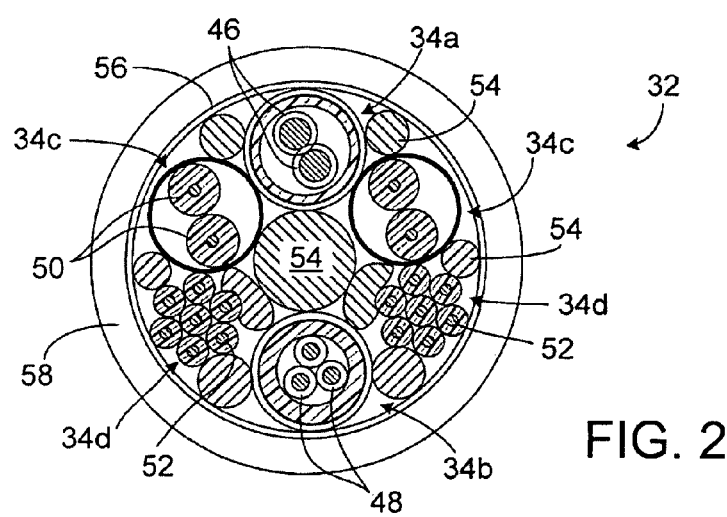
FIG. 2 is a cross-sectional view of a cable trunk of FIG. 1, taken along line 2-2.

FIG. 2 shows one implementation of an arrangement of wires within trunk cable 32. (For simplicity, the wires contained within trunk cable 32 are also designated by reference number 34, and specific wires within the trunk cable are designated according to the wires at the subject end 30 to which they are connected, i.e., wires 34a-34d.) Wires 34 include wire 34a, which includes two high voltage conductors 46 capable of defibrillation and/or cardiac pacing pulses. In some implementations, high voltage wire 34a includes two 22 AWG 19/34 silver-plated copper (SPC) conductors with 0.010 nominal fluoropolymer (twinned). Wire 34a may include 0.014 nominal wall fluoropolymer tape, 0.0015 aluminized polyester tape (foil out, with 40% nominal overlap), and 40 AWG SPC served shield (95% nominal coverage) to reduce interference and provide a good signal. The jacket may be 0.004 nominal wall fluoropolymer tape.

For ECG monitoring, wires 34 further include wire 34b, which includes three shielded conductors 48. As shown, ECG wire 34b (which is used for low current monitoring) and high voltage wire 34a (which may carry the most current during use) are spaced as far apart as possible within trunk cable 32 to reduce interference. In some implementations, ECG wire 34b includes three 28 AWG 7/36 tinned copper conductors with 0.010 nominal wall low-density polyethylene (LDPE). Wire 34b may include 0.015 wall fluoropolymer tape and 40 AWG SPC spiral shield. The jacket may be 0.004 nominal wall fluoropolymer.

Wires 34 farther include two $SpO_2$ wires 34c for oxygen monitoring and two CPR assistance wires 34d. As shown, each $SpO_2$ wire 34c includes two shielded conductors 50. For example, in some implementations, each $SpO_2$ wire 34c includes two 28 AWG 7/36 tinned copper conductors (100 ohm shielded twisted pair) with 0.020 nominal wall LDPE (twinned). Each wire 34c further includes 44 AWG tinned copper spiral shield, and a 0.004 nominal wall fluoropolymer tape jacket. In addition to providing CPR assistance, wires 34d are also capable of connecting to an electrode condition sensor and passing data code and identification information. As shown, each CPR assistance wire 34d includes a bundle of seven unshielded conductors 52 such as, for example, 32 AWG 7/40 SPC conductors with 0.010 nominal wall fluoropolymer. [Conductors 52 are unshielded because they do not carry low level signals.

In addition to wires 34, trunk cable 32 further contains multiple elongated segments of filler 54 extending along the length of the trunk cable. Filler 54 spaces wires 34 apart to reduce interference, and provides cable 26 with flexibility and a selected form (such as the shown circular cross section), particularly when the wires in the trunk cable have different widths or diameters. Filler 54 may also serve to reduce the total capacitance of cable 26. In some implementations, filler 54 includes polyvinylchloride (PVC). The assembly of wires 34 and filler 54 is wrapped with tape 56 (such as 0.002 fluoropolymer tape, 40% overlap) and a casing 58 (such as 0.041 nominal wall PVC) to complete trunk cable 32. A detailed construction of an implementation of cable 26 is provided below.

Cable 26 can be formed in a length sufficient to extend from medical device 20 to subject 22. Medical device 20 can be adapted to be mounted, for example, on a crash cart or on a gurney, or adapted to be hand carried or wall mounted. In some implementations, trunk cable 32 has a length from about six to about eight feet. The diameter of trunk cable 32 can vary, depending on what monitoring functions the trunk cable includes. As an example, a trunk cable not including EtCO2, NIBP, IBP and temperature monitoring may have a diameter of from about 0.25 inch to about 0.50 inch.

Figure 3:
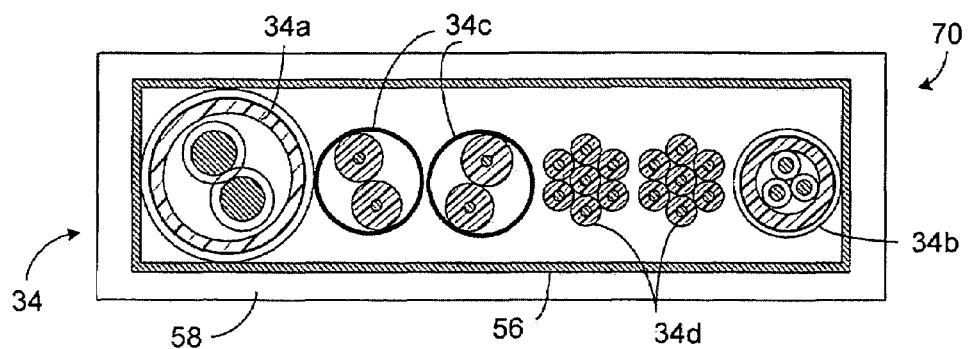
FIG. 3 is a cross-sectional, somewhat diagrammatic view of another implementation of the cable trunk.
Figure 4:
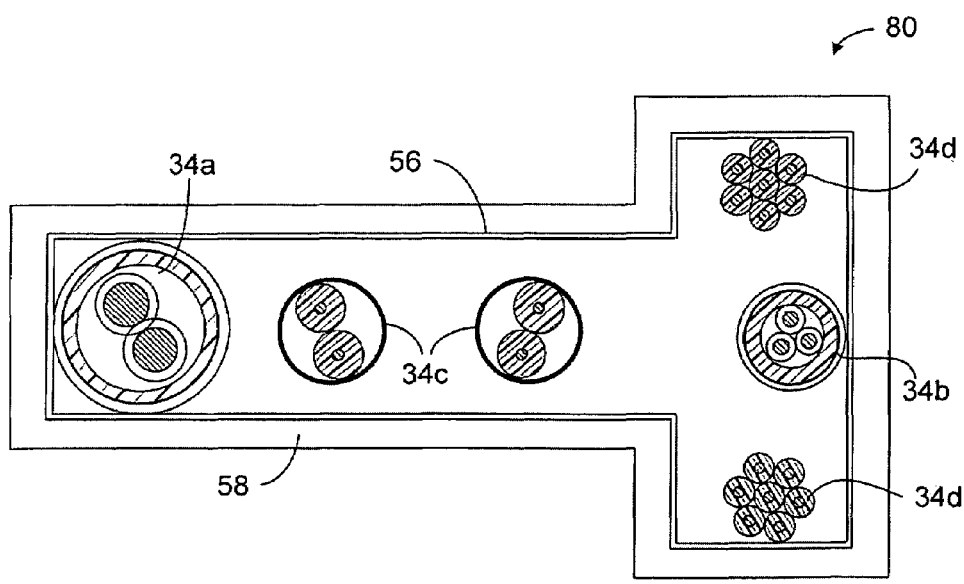
FIG. 4 is a cross-sectional, somewhat diagrammatic view of another implementation of the cable trunk.

While cable 26 is described above as having a circular cross section, in other implementations, cable 26 has a non-circular cross section. For example, referring to FIG. 3 (in which filler 54 is not shown), cable 70 has a rectangular cross section in which wires 34 are arranged linearly. FIG. 4 shows another implementation in which cable 80 has a T-shaped cross section. As shown, cables 70, 80 do not include filler material between wires 34 because the outer jacket of the cables serves to position the wires relative to each other. The outer jacket may be a preformed material with cavities or lumens extending along the length of the cable, and wires 34 may be placed in the appropriate lumens.

In use, the circuitry within housing 24 of medical device 20 can provide its therapeutic and monitoring functions in the conventional way. However, instead of providing these functions through multiple cables, medical device 20 can provide at least one therapeutic function and at least one monitoring function through a single cable 26.

Many other implementations other than those described above are within the invention, which is defined by the following claims. As mentioned earlier, it is not possible to describe here all possible implementations of the invention, but a few possibilities not mentioned above include the following.

The multi-function cables described herein need not include only electrical wires. For example, a multi-function cable can include a hose for an air coupling to perform oscillometric non-invasive blood pressure monitoring.

Figure 5:
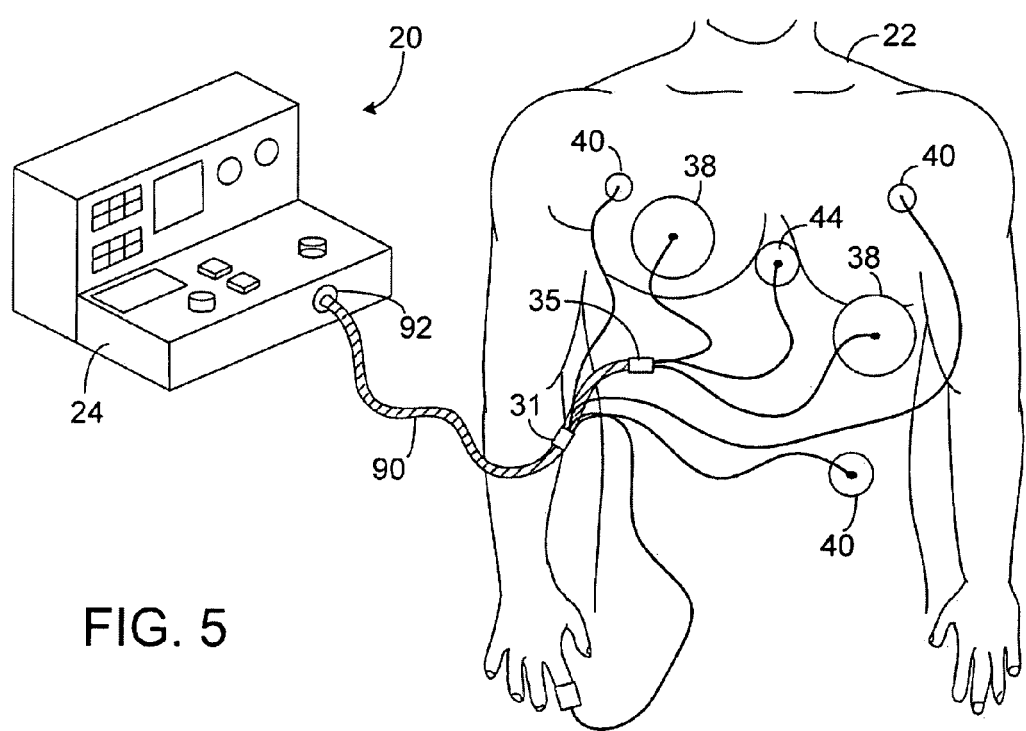
FIG. 5 is a diagrammatic view of another implementation of the cable during use.

For example, referring to FIG. 5, a multi-function cable 90 may be connected to medical device 20 with a single connector 92 to further facilitate connection and disconnection of the cable to the defibrillator.

Figure 6:
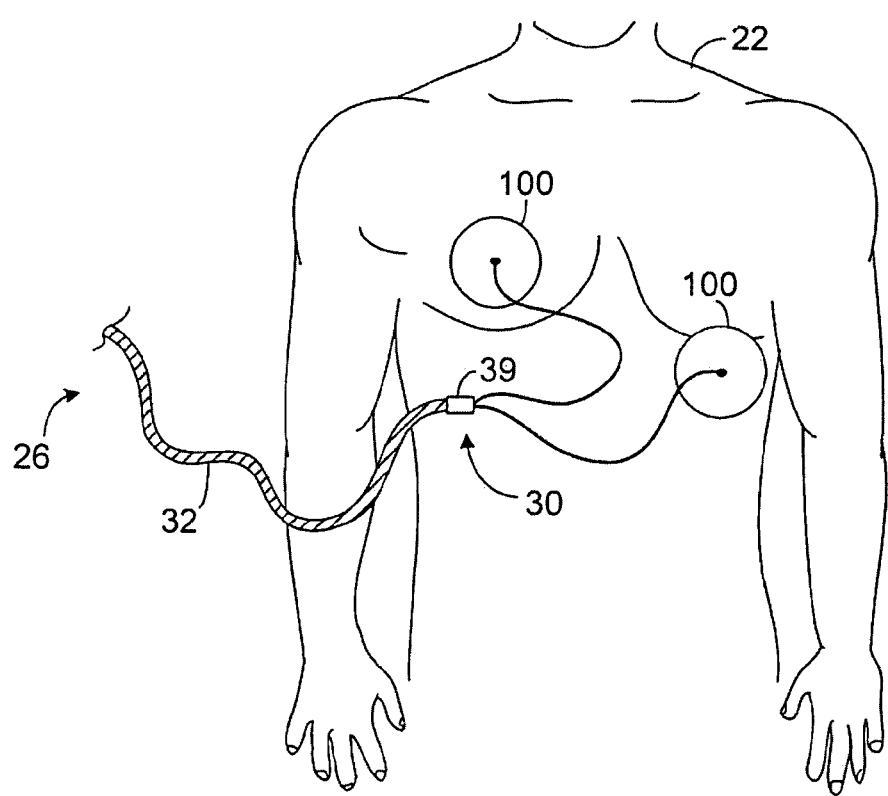
FIG. 6 is a diagrammatic view of another implementation of the cable during use.

Referring to FIG. 6, in some implementations, wires 34 in cable 26 can terminate with a single connector 39 at the patient end 30. Connector 39 is configured to connect to disposable electrodes 100, which are capable of performing one or more therapeutic functions (such as defibrillation and/or pacing) and one or more monitoring functions (such as CPR monitoring, ECG and/or pulse oximetry). Examples of electrodes 100 are described in commonly assigned U.S. Ser. No. 11/055572, filed concurrently with this application and entitled "Monitoring Physiological Signals During External Electrical Stimulation", hereby incorporated by reference.

In some implementations, the multi-function cable may include a fastener (such as a clip) near the subject's end 30 to hold the cable in place (e.g., to the patient's gown, clothing, or bedding) during use. The fastener can be placed, for example, at yoke 31.

In some implementations, only selected functionalities of a medical device are integrated into a single cable, i.e., not all of the functionalities of a medical device need to be integrated into a single cable. For example, a medical device may be configured to perform two therapeutic functions and five monitoring functions, and the therapeutic functions can be integrated into a single cable with three monitoring functions. The remaining two monitoring functions may be performed with two other cables. As a result, three cables may extend from the medical device to the subject, rather than, for example, six cables extending from the device.

Medical device 20 can be a single unit capable of performing the therapeutic function(s) and monitor function(s), or the device can include multiple units to perform these functions

What is claimed is:

1. A cable configured for use between a medical device and a subject, comprising:
    a first end configured to connect to the medical device;
    a second end configured to connect to the subject; and
    a single elongated body between the first and second ends, the body containing a first set of conductors configured to deliver a therapeutic current to the subject, and a second set of conductors configured to perform a first monitoring function.

2. The cable of claim 1, wherein the therapeutic current delivered is defibrillation and/or cardiac pacing current.

3. The cable of claim 1, wherein the first set of conductors is electromagnetically shielded.

4. The cable of claim 1, wherein the first monitoring function is selected from the group consisting of oxygen monitoring, carbon dioxide monitoring, blood pressure monitoring, cardiopulmonary resuscitation assistance, electrocardiographing, and temperature monitoring.

5. The cable of claim 1, wherein the second set of conductors is electromagnetically shielded.

6. The cable of claim 1, wherein the elongated body contains multiple sets of conductors configured to perform different monitoring functions.

7. The cable of claim 6, wherein the cable is configured to perform defibrillation, pacing, oxygen monitoring, cardiopulmonary resuscitation assistance, and electrocardiographing.

8. The cable of claim 1, further comprising a filler material extending along the length of the elongated body.

9. The cable of claim 8, wherein the first set of conductors has a first width, the second set of conductors has a second width different than the first width, and the filler material is between the first and second sets of conductors.

10. The cable of claim 1, wherein the body has a non-circular cross section.

11. The cable of claim 1, wherein the first end comprises a single connector configured to connect to the medical device.

12. The cable of claim 1, wherein the first end comprises a plurality of connectors configured to connect to the medical device.

13. The cable of claim 1, wherein the body has a length of from about six to about eight feet.

14. The cable of claim 1, further comprising a fastener attachable to the cable.

15. A cable configured for use between a medical device and a subject, comprising:
    a first end configured to connect to the medical device;
    a second end configured to connect to the subject; and
    a single elongated body between the first and second ends, the body containing a first set of conductors configured to carry current to perform cardiopulmonary resuscitation assistance, and a second set of conductors configured to perform a first monitoring function.

16. The cable of claim 15, wherein the first set of conductors is configured to connect to an accelerometer.

17. The cable of claim 15, wherein the first monitoring function is selected from the group consisting of oxygen monitoring, carbon dioxide monitoring, blood pressure monitoring, electrocardiographing, and temperature monitoring.

18. The cable of claim 15, wherein the second set of conductors is electromagnetically shielded.

19. The cable of claim 15, wherein the body contains multiple sets of conductors configured to perform different monitoring functions.

20. The cable of claim 15, further comprising a filler material extending along the length of the body.

21. The cable of claim 15, wherein the body has a non-circular cross section.

22. The cable of claim 15, wherein the first end comprises a single connector configured to connect to the medical device.

23. The cable of claim 15, wherein the first end comprises a plurality of connectors configured to connect to the medical device.

24. The cable of claim 15, wherein the body has a length of from about six to about eight feet.

25. A method of providing therapy to and monitoring a subject, the method comprising delivering a therapeutic electrical pulse and monitoring a parameter of the subject through a single multi-conductor cable connected to and extending between the subject and a medical device, wherein the therapeutic electrical pulse is delivered through at least one of the conductors of the cable, and the parameter is monitored using at least another of the conductors of the cable.

26. The method of claim 25, wherein electrical pulse is a defibrillation pulse or a cardiac pacing pulse.

27. The method of claim 25, wherein the parameter is selected from the group consisting of oxygen monitoring, carbon dioxide monitoring, blood pressure monitoring, cardiopulmonary resuscitation assistance, electrocardiographing, and temperature monitoring.

* * * * *